United States Patent [19]

Keith

[11] Patent Number: 4,980,150
[45] Date of Patent: Dec. 25, 1990

[54] CHLORHEXIDINE COMPLEX
[75] Inventor: Alec D. Keith, State College, Pa.
[73] Assignee: Zetachron, Inc., State College, Pa.
[21] Appl. No.: 344,257
[22] Filed: Apr. 27, 1989
[51] Int. Cl.$^5$ .............................................. A61K 7/16
[52] U.S. Cl. ........................................ 424/49; 536/3;
424/78; 514/54; 514/779; 514/901; 514/781
[58] Field of Search ................... 536/3; 424/49, 78;
514/54, 779, 901, 781

[56]  References Cited
U.S. PATENT DOCUMENTS

| | | | |
|---|---|---|---|
| 3,842,168 | 10/1974 | Colodney | 424/52 |
| 3,956,480 | 5/1976 | Dichter et al. | 424/49 |
| 4,289,749 | 9/1981 | Keith et al. | 424/449 |
| 4,393,219 | 7/1983 | Inoue et al. | 548/534 |
| 4,569,837 | 2/1986 | Suzuki et al. | 424/435 |
| 4,666,896 | 5/1987 | Walter, Jr. et al. | 514/114 |
| 4,857,303 | 8/1989 | Grollier | 424/49 |
| 4,877,617 | 10/1989 | Namikoshi et al. | 536/3 |

*Primary Examiner*—Ronald W. Griffin
*Attorney, Agent, or Firm*—Webb, Burden, Ziesenheim & Webb

[57] ABSTRACT

A chlorhexidine complex is prepared by complexing chlorhexidine (a divalent, cationic antiseptic) with an anionic polymer such as algin or carboxymethylcellulose. The complex is insoluble but can be granulated or crushed to a fine powder. In powdered form the complex forms stable aqueous dispersions. The chlorhexidine complex is suitable for inclusion in oral hygiene compositions such as dentrifrices, and in other antibacterial compositions such as opthalmic under-eye-lid treatment capsules topical preparations and ocular solutions.

7 Claims, No Drawings

CHLORHEXIDINE COMPLEX

FIELD OF THE INVENTION

The present invention relates to antibacterial compositions containing chlorhexidine, and more particularly relates to a chlorhexidine complex which, when included in an oral hygiene composition, avoids the bad taste and tooth enamel staining disadvantages characteristic of prior art chlorhexidine-containing compositions.

BACKGROUND OF THE INVENTION

Benefits attributable to the inclusion of chlorhexidine in oral hygiene compositions have been widely documented in the literature. For example, Loe, Harald, ed., in Supplement No. 16, Vol. 21, 1986 to the *Journal of Periodontal Research*, presents seven published articles collectively entitled "Chlorhexidine in the Prevention and Treatment of Gingivitis." The Loe Supplement discusses various aspects of oral hygiene including: the effect of chlorhexidine gluconate mouth rinse on plaque bacteria; the efficacy of oral rinsing with chlorhexidine digluconate as compared with phenolic and plant alkaloid compounds; the results of a sixmonths' study of the effects of a chlorhexidine mouth rinse on gingivitis in adults; and other related topics. The Loe Supplement is representative of numerous published reports concerning the inclusion of chlorhexidine in oral hygiene compositions such as dentifrices and rinses.

Oral compositions containing chlorhexidine are also documented in the patented literature. For example, U.S. Pat. No. 3,842,168 to Colodney, entitled "Method of Preparing Stable Dentifrice," discloses a method of stabilizing a dentifrice containing alkali metal carboxyalkyl cellulose and 1,6-di-(p-chlorophenyl biguanidohexane) salt (i.e., chlorhexidine salt) against precipitation and flocculation. Also, U.S. Pat. No. 4,569,837, entitled "Pharmaceutical Preparation for Remedy of Periodontal Disease and Process for Production Thereof," discloses films which contain and release chlorhexidine gluconate and are suitable for insertion in the gingival sulcus.

Antibacterial compositions not intended for oral hygiene use may also contain chlorhexidine in various forms. For example, U.S. Pat. No. 4,666,896 to Warner, Jr. et al. discloses dermatological compositions containing water insoluble dinalidixate or diphosphanilate chlorhexidine salts. The insoluble salts are milled to a fine particle size and are dispersed within the compositions.

Unfortunately, when chlorhexidine (or one of its salts) is incorporated in an oral hygiene composition, the resultant product almost invariably has a strong, foul, bitter taste which flavoring agents can only partially mask. In addition, chlorhexidine (or one of its salts) stains tooth enamel an unsightly brown color, and the stains are resistant to removal by most if not all consumer dentifrices. These disadvantages present serious obstacles to the development of a product which provides optimal application of chlorhexidine to the mouth, teeth and gingiva, maintains cosmetic integrity of the tooth enamel, and avoids the foul taste of other chlorhexidine-containing compositions.

SUMMARY OF THE INVENTION

The present invention is a chlorhexidine complex which, when added to oral hygiene compositions, provides the benefits of chlorhexidine application without the attendant disadvantages of enamel staining and bad taste. Furthermore, the chlorhexidine complex provides a chemically and physically stable form of chlorhexidine which is particularly suited for inclusion in a paste-type professional dentifrice or a consumer tooth paste product, as well as in surgical scrubs, ocular solutions and other antibacterial compositions. The present chlorhexidine complex is prepared by complexing chlorhexidine (a divalent, cationic antiseptic) with an anionic polymer, such as algin or carboxymethylcellulose, and pulverizing the resultant precipitate into granules or a powder suitable for inclusion in oral hygiene and other compositions. The powdered form of the complex may be pulverized finely enough to form stable aqueous dispersions.

DETAILED DESCRIPTION OF THE INVENTION

Chlorhexidine, or 1,6-di-(p-chlorophenyl biguanidohexane) has the following chemical structure:

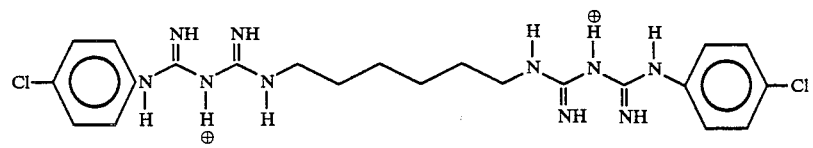

and accordingly has a molecular weight of 505.48. In its free base form, chlorhexidine readily forms salts including chlorhexidine gluconate, chlorhexidine acetate, chlorhexidine diacetate, chlorhexidine fluoride, chlorhexidine digluconate, chlorhexidine dihydrogen fluoride and the like. The above salts are examples of chlorhexidine compounds which have at this writing already exhibited significant broad-spectrum antibacterial activity both in vitro and in vivo.

Unlike typical chlorhexidine salts, however, the present chlorhexidine complex is an insoluble ionic complex between chlorhexidine and an anionic polymer such as algin or carboxymethylcellulose. Other suitable anionic polymers include anionic acetate polymers, anionic acrylic polymers and other anionic methylcellulose (i.e., hydroxypropylmethylcellulose), ethylcellulose and propylcellulose (i.e., hydroxypropylcellulose) polymers. When the insoluble ionic complex is prepared, as described below, a precipitate results which is insoluble not only in water but also in alcohol and in strong organic solvents. The precipitate can be granulated or pulverized to a fine powder, and the granulated or powdered complex is suitable for inclusion in dentifrices and other oral hygiene compositions. For example, the complexes are easily pulverized to a particle size which permits stable dispersion thereof in water, and granules or powders of the complex can be admixed with paste compositions.

The present chlorhexidine complexes must be distinguished from polymers or films containing free chlorhexidine (or chlorhexidine salts) in a dispersion matrix or other slow- or sustained-release matrix. The present complexes are not mere physical admixtures of the constituents but are instead ionic complexes, i.e., complexes formed at the molecular ionic level. Chlorhexidine complexes according to the present invention are therefore always prepared as insoluble precipitates, and it is believed (without intention of being bound thereby) that the complexing of the chlorhexidine in an insoluble precipitate, prior to inclusion of the chlorhexidine complex in an oral hygiene composition, results in the avoidance of the tooth staining and bad taste associated with prior art chlorhexidine compositions. The complexes are also chemically and physically stable.

Generally, the present chlorhexidine complexes are prepared by titration in aqueous medium at room temperature. A water-dissociable salt of chlorhexidine is dissolved in an excess of water, and a stoichiometric excess of an aqueous solution of a water-dissociable salt of the selected anionic polymer is added to the aqueous chlorhexidine with stirring. Although the complexation can be carried out with stoichiometrically equivalent amounts of chlorhexidine and anionic polymer, such a titration is difficult to carry out and takes a long time. Therefore, use of a stoichiometric excess of the anionic polymer (most preferably, on the order of at least about two equivalents thereof) is preferred.

After the complexation of chlorhexidine and anionic polymer occurs, the resulting precipitate can be removed from solution by means known in the art, i.e., filtration, centrifugation or the like. In order to facilitate granulation and/or pulverization, the precipitate is generally dried in a 70° C. oven prior to granulation or pulverization by means known in the art.

Specific processes for complexing chlorhexidine with anionic polymers are set forth in the Examples below. Also described in the Examples are test results which indicate that the antimicrobial activity of chlorhexidine is either insignificantly affected or unaffected by its complexation according to the present invention. Oral hygiene compositions may therefore be prepared by including roughly the same chemically equivalent amount of one or more of the present chlorhexidine complexes as would have been included had prior art chlorhexidine salts been used.

EXAMPLE I

Chlorhexidine diacetate and sodium alginate were used to prepare a chlorhexidine alginate complex as follows. Sodium alginate, having the repeating unit

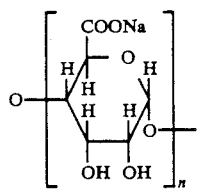

and a unit molecular weight of 175, was selected as the anionic polymer for complexation. The equivalent weight equalled 350, i.e., the molecular weight of two units n. The molecular weight for the sodium alginate polymer was on the order of 8,000–12,000.

Chlorhexidine diacetate, in the amount of fifty (50) parts by weight, was dissolved in 300 parts by weight of water. Seventy (70) parts by weight of sodium alginate (i.e., approximately two equivalents) were dissolved in 2,000 parts by weight of water. The sodium alginate solution was added to the chlorhexidine diacetate solution with stirring. Clouding of the admixed solutions indicated formation of a water-insoluble complex between the free chlorhexidine and the free algin. Ultimately, 964 parts by weight of a chlorhexidine alginate precipitate formed. The precipitate was filtered from solution, was dried at 70° C. for about one hour, and was granulated.

Growth plates containing "lawns" of *E. coli* were sparsely seeded with chlorhexidine alginate complex granules prepared as above. Identical *E. coli* growth plates were separately contacted, at wide intervals, with applications of a roughly equivalent amount of chlorhexidine diacetate (i.e., about one-fifth the amount by weight of the weight of the chlorhexidine alginate complex granule). Both the complex granules and the chlorhexidine diacetate applications yielded, over the same period of time, "no-growth" zones on the *E. coli* lawns which were by all appearances the same.

EXAMPLE II

The process according to Example I was repeated except that the total aqueous admixed system contained 0.3% by weight chlorhexidine diacetate, 3% carboxymethylcellulose (having a molecular weight of about 200), and 20% ethanol. A chlorhexidine carboxymethylcellulose complex formed, precipitated from solution, and was filtered, dried, and granulated.

EXAMPLE III

Chlorhexidine dihydrochloride and sodium alginate were used to prepare a chlorhexidine complex. Fifty parts by weight of chlorhexidine dihydrochloride were dissolved in 300 parts by weight of water. Seventy parts by weight of sodium alginate were dissolved in 2,000 parts by weight of water. The sodium alginate solution was added to the chlorhexidine dihydrochloride solution with stirring. Clouding of the admixed solutions indicated formation of a water-insoluble complex between the free chlorhexidine and the free algin. The precipitate was filtered from solution, was dried at 70° C. for about 1 hour and was granulated.

EXAMPLE IV

Serial dilutions of the chlorhexidine carboxymethylcellulose complex prepared according to Example II were prepared by pulverizing the chlorhexidine carboxymethylcellulose complex precipitate, dispersing the pulverized complex in water, and confirming the stability of the dispersion. Serial dilutions of Peridex ®, a commercially available antimicrobial solution of chlorhexidine gluconate, were also prepared in water. The chlorhexidine free base percent by weight was the same for all dilutions. Identical amounts of the diluted solutions were dropped, using sterile technique, onto identical lawns of *E. coli* on growth plates. "No-growth" areas on the *E. coli* lawns were measured in millimeters, and all measurements were made after 24 hours' standard *E. coli* incubation. The findings of this experiment are summarized in Table I.

TABLE I

Comparative Size of No-Growth Areas of *E. coli* Treated with Equivalent Dilutions of Chlorhexidine Carboxymethylcellulose Complex (CH:CMC) and Peridex ®, Respectively.

| PERCENT CHLOR- HEXIDINE FREE BASE | DIAMETER (IN MM) OF NO-GROWTH ZONE SURROUNDING CH:CMC | DIAMETER (IN MM) OF NO-GROWTH ZONE SURROUNDING PERIDEX ® |
|---|---|---|
| 0.0677 | 15 (mm.) | 16 |
| 0.0200 | 12 | 11 |
| 0.0100 | 10 | 10 |
| 0.0050 | 8 | 9 |
| 0.0020 | 8 | 8 |
| 0.0010 | 7 | 7 |
| 0.0005 | 5* | 5* |
| 0.0002 | 5* | 5* |

*initial no-growth followed by regrowth.

EXAMPLE V

The process according to Example I was repeated except that the total aqueous admixed system contained 0.3% by weight chlorhexidine dihydrochloride, 3% carboxymethylcellulose and 20% ethanol. A chlorhexidine carboxymethylcellulose complex formed, precipitated from solution, and was filtered, dried and granulated.

A toothpaste was made with the following composition:

Sorbitol: 35.00%
Silox 15: 10.00%
Syloid 750: 10.00%
Na CM: 1.60%
SLS: 1.50%
Flavor: 2.00%
MFP: 0.75%
Na Benzoate: 0.50%
TiO$_2$: 0.50%
Na Saccharin: 0.20%
Chlorhexidine Complex: 0.11%
Blue No. 1: 0.0027%
Water: to 100%

The toothpaste formulation was used by several subjects on a regular daily basis for various periods up to one month. None of the subjects reported experiencing objectionable flavor or staining of the teeth, in the course of routine monitoring of the subjects.

EXAMPLE VI

The solutions (dilutions) used in Example IV (Table I) were prepared under sterile conditions and charged, individually, to sterile cell culture tubes in aliquots of several milliliters each. Several control tubes were partially filled with sterile 5% saline. All tubes contained the same amounts of various growth media constituents, known in the art, expedient in the colonization of *Streptococcus mutans*.

One end of each of several sterile glass rods was inoculated with *S. mutans* by coating each rod end with the same amount of human saliva (collected in a single specimen from a single donor). One rod was placed, inoculated end down, in each of the prepared tubes. All tubes were incubated at 36° C. for 24 hours.

At the end of the incubation period, the rod ends were examined visually for *S. mutans* plaque accumulation. Gross plaque deposits appeared on all control rods. Lesser and visually equal amounts of plaque formation were observed between tubes containing equivalent dilutions of chlorhexidine, regardless of whether the chlorhexidine was attributable to Peridex ® or to the chlorhexidine carboxymethylcellulose complex prepared in accordance with Example II.

Although the invention has been described particularly above, the invention is only to be limited insofar as is set forth in the accompanying claims. For example, the claimed complex may be included in small opthalmic anti-infective polymer capsules or matrices, for placement under the eyelid, or may be finely milled and suspended in eye drop dispersions. Alternately, about 1-4% of the present chlorhexidine complex may be present in surgical scrub compositions, in dispersed particulate form. The present complex may be included in masticable matrices including lozenges, chewing gum, sticks (popsicle sticks, toothpicks, dental stimulators), chewable tablets, foams, pads, brushes or beads.

I claim:

1. An antibacterial composition, comprising:
   an amount of an ionic complex, of chlorhexidine and an anionic polymer, effective to inhibit microorganism viability upon application of said complex to human tissue selected from the group consisting of dermis and mucosa,
   a pharmaceutically acceptable excipient therefore, and
   the antibacterial composition being characterized by its ability to contact human oral mucosa without eventuating bitter taste.

2. The antibacterial composition according to claim 1 wherein said anionic polymer is selected from the group consisting of algin, anionic cellulose polymers, anionic acetate polymers and anionic acrylic polymers.

3. The antibacterial composition according to claim 1 wherein said anionic polymer is selected from the group consisting of algin, carboxymethylcellulose, hydroxypropylmethylcellulose and hydroxypropylcellulose.

4. The antibacterial composition according to claim 3 wherein said ionic complex is insoluble and is in powdered form.

5. The antibacterial composition according to claim 3 wherein said ionic complex is further characterized by its ability to contact human oral mucosa without staining human enamel at all or to a lesser degree than free chlorhexidine stains human enamel.

6. The antibacterial composition according to claim 5 wherein said pharmaceutically acceptable excipient further comprises a dentifrice composition, within which said ionic complex is stably dispersed.

7. The antibacterial composition according to claim 5 wherein said pharmaceutically acceptable excipient further comprises an aqueous mouth rinse composition, within which said ionic complex is stably dispersed.

* * * * *